(12) United States Patent
Rappel et al.

(10) Patent No.: US 9,392,258 B2
(45) Date of Patent: Jul. 12, 2016

(54) IMAGING SYSTEM AND METHOD

(75) Inventors: James Kolenchery Rappel, Singapore (SG); Timothy Poston, Singapore (SG); Beng Hai Lim, Singapore (SG)

(73) Assignee: National University of Singapore, Singapore (SG)

( * ) Notice: Subject to any disclaimer, the term of this patent is extended or adjusted under 35 U.S.C. 154(b) by 397 days.

(21) Appl. No.: 13/983,193

(22) PCT Filed: Feb. 1, 2012

(86) PCT No.: PCT/SG2012/000029
§ 371 (c)(1),
(2), (4) Date: Aug. 1, 2013

(87) PCT Pub. No.: WO2012/105909
PCT Pub. Date: Aug. 9, 2012

(65) Prior Publication Data
US 2013/0307935 A1    Nov. 21, 2013

(30) Foreign Application Priority Data
Feb. 1, 2011   (SG) .................................. 201100758

(51) Int. Cl.
*H04N 13/02* (2006.01)
*A61B 1/00* (2006.01)
(Continued)

(52) U.S. Cl.
CPC ........ *H04N 13/0203* (2013.01); *A61B 1/00048* (2013.01); *A61B 8/0841* (2013.01);
(Continued)

(58) Field of Classification Search
CPC .......... H04N 13/0239; H04N 13/0055; H04N 13/0296; H04N 13/0497; H04N 13/0242; H04N 13/0022; H04N 2013/0081; H04N 13/0029; H04N 13/0066; H04N 13/0011; H04N 13/0217; H04N 9/8227; H04N 13/0048; H04N 13/0438
See application file for complete search history.

(56) References Cited

U.S. PATENT DOCUMENTS

| 2006/0013447 A1* | 1/2006 | Siegel ................ G06K 9/00013 382/115 |
| 2006/0020204 A1* | 1/2006 | Serra .................... A61B 8/0833 600/437 |

(Continued)

FOREIGN PATENT DOCUMENTS

| WO | WO-2008/100229 A1 | 8/2008 |
| WO | WO-2012/105909 A1 | 8/2012 |

OTHER PUBLICATIONS

"International Application No. PCT/SG2012/000029, International Search Report mailed Apr. 23, 2012", 6 pgs.
(Continued)

*Primary Examiner* — Sath V Perungavoor
*Assistant Examiner* — Howard D Brown, Jr.
(74) *Attorney, Agent, or Firm* — Schwegman Lundberg & Woessner, P.A.

(57) ABSTRACT

There is provided an imaging system comprising image capture apparatus and display apparatus. The image capture apparatus is for capturing an image of an operator work site, the image including depth information. The display apparatus is in communication with the image capture apparatus, and comprises at least one display screen. The display apparatus is arranged to receive the image captured by the image capture apparatus, including the depth information, and display to the operator the image captured by the image capture apparatus, including the depth information, on the display screen. The display screen is located between the operator's eyes and the position of the work site. There is also provided a method for capturing and displaying an image of an operator work site.

24 Claims, 5 Drawing Sheets (51) Int. Cl.
  *G02B 21/22* (2006.01)
  *H04N 13/00* (2006.01)
  *H04N 13/04* (2006.01)
  *A61B 8/08* (2006.01)
  *A61B 8/00* (2006.01)

(52) U.S. Cl.
  CPC ............... *A61B 8/461* (2013.01); *A61B 8/467* (2013.01); *G02B 21/22* (2013.01); *H04N 13/004* (2013.01); *H04N 13/0271* (2013.01); *H04N 13/0278* (2013.01); *H04N 13/044* (2013.01); *H04N 13/0484* (2013.01); *A61B 8/468* (2013.01)

(56) References Cited

U.S. PATENT DOCUMENTS

| | | | | |
|---|---|---|---|---|
| 2006/0097176 A1* | 5/2006 | Szu | ..................... | A61B 5/0059 250/370.08 |
| 2007/0032906 A1* | 2/2007 | Sutherland | ............. | A61B 19/22 700/248 |
| 2008/0260225 A1* | 10/2008 | Szu | ........................ | A61B 5/015 382/128 |
| 2010/0103247 A1* | 4/2010 | Lim | ........................ | A61B 19/52 348/47 |
| 2010/0321482 A1* | 12/2010 | Cleveland | ................ | G06F 3/012 348/78 |
| 2012/0218236 A1* | 8/2012 | Hirose | ................... | G09G 3/003 345/204 |
| 2012/0262452 A1* | 10/2012 | Tadao | ................. | G02B 27/2264 345/419 |
| 2012/0287065 A1* | 11/2012 | Oshinome | ............. | G06F 3/0488 345/173 |

OTHER PUBLICATIONS

"International Application No. PCT/SG2012/000029, Written Opinion mailed Apr. 23, 2012", 7 pgs.

"International Application Serial No. PCT/SG2012/000029, International Preliminary Report on Patentability dated Aug. 6, 2013", 8 pgs.

Fife, K., et al., "A 3MPixel Multi-Aperture Image Sensor with 0.7 µm Pixels in 0.11 µm CMOS", *IEEE ISSCC Digest of Technical Papers* (Feb. 2008), 48-49, 594.

\* cited by examiner

IMAGING SYSTEM AND METHOD

PRIORITY CLAIM TO RELATED APPLICATIONS

This application is a national stage application under 35 U.S.C. §371 of PCT/SG2012/000029, filed Feb. 1, 2012, and published as WO 2012/105909 A1 on Aug. 9, 2012, which claims priority to Singapore Application No. 201100758-0, filed Feb. 1, 2011, which applications and publication are incorporated by reference as if reproduced herein and made a part hereof in their entirety, and the benefit of priority of each of which is claimed herein.

FIELD OF THE INVENTION

The present invention relates to the fields of microscopy and digital interaction and display. In particular, the present invention relates to an imaging system for capturing and displaying an image of an operator work site.

BACKGROUND TO THE INVENTION

Seeing small objects enlarged, and working on those objects, began with the lens. A large lens presents paired distinct views (a stereo image) to the two eyes of an operator, and a change in view (parallax) when the operator's head moves. These two depth cues are powerful for the human vision system, and enable the operator to obtain a strong three-dimensional sense of the object behind the lens. Such depth cues are important if the operator is to manipulate objects such as tools. It must be possible to position a tool correctly in the depth direction, as well as move the tool correctly across the image in the length and width directions.

Subsequently, the microscope, combining multiple lenses and other elements, brought greater enlarging power, but at the cost of poorer depth cues. Since the operator must place an eye exactly at the eyepiece, head motion needed for parallax is not possible. The standard single eyepiece microscope also provides only one view. Although weaker depth cues, such as a near object obscuring a more distant object, may still be provided to the operator, positioning a tool, precisely in the depth direction may not be possible. The binocular microscope, which provides two eyepieces but which provides the same view to both eyes, brought extra comfort for the operator because there is no need to cover or shut the second eye or ignore that eye's view. However, the human brain can still not reconstruct depth, and guiding micro-tools remains difficult.

The stereo microscope uses two separate optical paths with two objectives and two eyepieces to provide slightly different viewing angles to the left and right eyes of an operator. The stereo microscope restored binocular depth perception, but parallax remains unavailable, because the operator's head must remain stationary at the eyepieces. In addition, stereo depth perception is strong in only about half the population, so the stereo microscope brought good depth perception to only about half the users. Operators, such as micro-surgeons and those assembling microscopic electronic parts, without strong stereo depth perception, were still unable to use the stereo microscope effectively.

However, the microscope does maintain a key advantage of the simple lens: hand/eye co-location and hand/eye co-orientation. In a direct view, the visually perceived position of a hand or tool coincides almost exactly with the operator's neuromuscular sense of where it is, and in what direction its parts are oriented, through the proprioception of the operator's own joint positions. Such a match between apparent (viewed) and physical locations is referred to as hand/eye co-location. And, such a match between apparent (viewed) and physical orientations is referred to as hand/eye co-orientation. These are key requirements for guiding a tool. Enlargement necessarily sacrifices the locational match between perception and view to some extent, but the scene can still be centred on a common location. More importantly, every rotation has an axis direction and an angle of rotation, and these can match well between perception and the magnified view.

Figure 1:
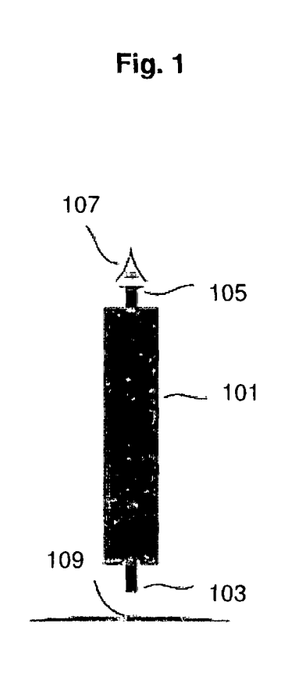
FIG. 1 is a schematic illustration of a vertical microscope according to the prior art.
Figure 2:
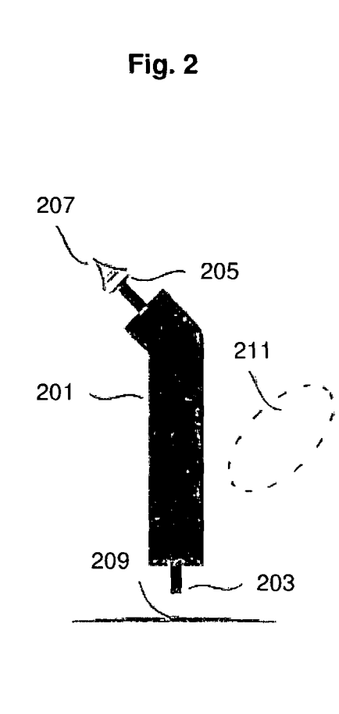
FIG. 2 is a schematic illustration of an indirect microscope according to the prior art.

FIG. 1 shows a surgical microscope 101, according to the prior art, in which the co-orientation is exactly preserved. The microscope 101 comprises an objective lens 103 and an eyepiece 105. The operator's eye or eyes 107 (shown in profile in FIG. 1) can see vertically down through eyepiece 105, to see an enlarged view of work site 109. However, most work is more comfortable with a tilted eyepiece, so that a sitting operator can look into the eyepiece easily. FIG. 2 shows an indirect microscope 201 according to the prior art. The microscope 201 comprises a vertical object lens assembly 203 and an angled eyepiece or eyepieces 205 for the operator's eye or eyes 207 (shown in profile in FIG. 2). A system of lenses and mirrors (not shown in FIG. 2) inside the microscope delivers the view of the work site 209 from the vertical object lens assembly 203 to the tilted eyepiece or eyepieces 205. In the microscope of FIG. 2, the orientations match imperfectly, and the visual location of the work site (shown schematically at 211, although the apparent distance depends on stereo adjustments) is moved substantially from its physical site 209. Operators may learn to overcome these obstacles, but they are not trivial.

Figure 3:
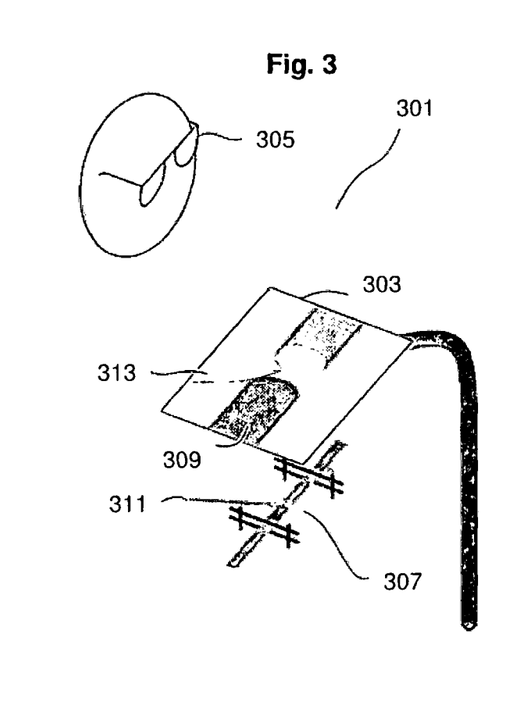
FIG. 3 shows an imaging system for magnified work, the system including a flat display screen, according to the prior art.

FIG. 3 shows an imaging system 301 according to WO 2008/100229, in the name of National University of Singapore, the disclosure of which is hereby incorporated by reference. In FIG. 3, the work site and its contents appear to the operator in substantially the same location and orientation as envisaged by the operator's motor cortex. Variations, for use with two collaborating operators, may be provided and will be described more fully with reference to FIGS. 4 and 5. In this specification, such a system, including the variations described below, will be referred to as a "flatscope". A display appears on a thin flat display screen 303, and the stereo view is achieved by alternating left and right views with synchronized shutter glasses 305, worn by the operator, to control which eye sees which view, or by a means of directing different view in different directions. The subject or operand 307 of the operator's actions, shown in FIG. 3 as a pair of artery ends to be joined, appears as an enlarged operand image 309 on the display screen 303. Similarly, any tool 311 held and operated by the operator appears as an enlarged tool image 313 on the display screen 303. The close match between apparent and real locations and the precise match between apparent and real orientations assists the operator. The replacement of an optical eyepiece by a larger display screen is not unique to the system shown in FIG. 3. However, the close match between hand and eye in perceived location is missing in some recently developed systems, which place the screen away from the line between the eye and the physical operand, and typically rotate it by as much as 90°. In this specification, systems with such major deviation from hand/eye co-location are excluded from the term "flatscope".

As shown in FIG. 3, a display screen is provided between the operator's physical work site and the operator's eyes. On the display screen, a magnified view of the work site appears to the operator in substantially the same location and orientation as it is envisaged by the operator's motor cortex. That is, there is no discrepancy between the physical and apparent locations of the work site and operand, as shown in FIG. 2.

Typically the magnification is up to fifteen times, not because of technical obstacles to higher magnification, but because hand tremor makes a closer view unhelpful. If a means to reduce tremor is used, the usable magnification factor increases. With indirect means of controlling tremor, such as the use of remotely controlled robot arms at a distant location, the hand/eye co-location is specifically between where the work site is seen to be by the operator and where it is felt to be by the operator's hands, without regard to the physical location of the work site. In a preferred implementation, the display screen is substantially orthogonal to the line of view, but appropriate construction of the view permits any angle at which the screen wholly covers the eyes' view of the work site and can be clearly seen.

Figure 4:
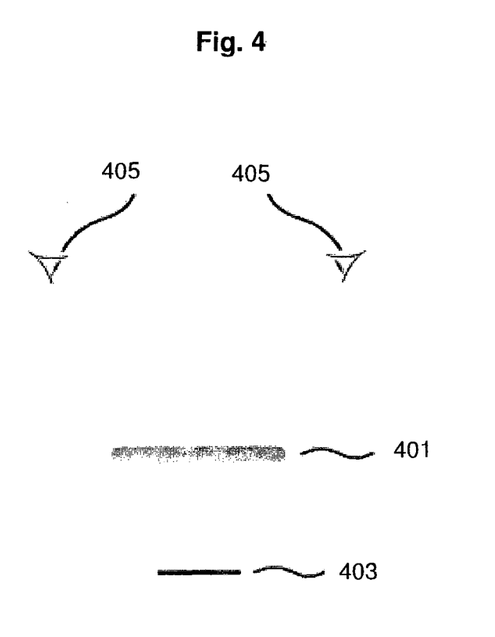
FIG. 4 is a schematic illustration of a single-user imaging system according to the prior art.
Figure 5:
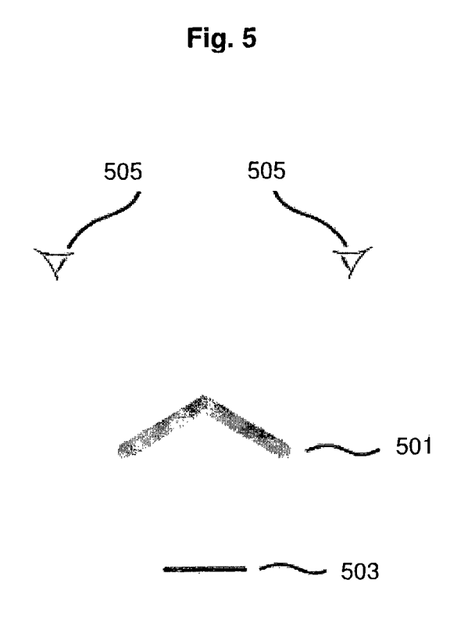
FIG. 5 is a schematic illustration of a two-user imaging system according to the prior art.

As already mentioned, two operators may collaborate and work on a shared magnified operand. This is particularly common among surgeons, where tasks such as suturing are easier with more than two hands. FIG. 4' is a schematic illustration of a single-user flatscope according to the prior art, which may be used by a plurality of collaborating operators. FIG. 4 shows a single display screen 401 located between the physical work site 403 and the eyes 405 of a plurality of operators. In FIG. 4, two operators are shown, but any number of operators may collaborate. FIG. 5 is a schematic illustration of a two-user flatscope according to the prior art. FIG. 5 shows two display screens 501 located between the physical work site 503 and the eyes 505 of two operators. Analogous placements for three or four operators will be evident to persons skilled in the art.

Hand/eye co-location involves not only a sense of the direction in which the operand lies, but a sense of the distance from the eyes of each object within the work site; this is referred to as "depth". Some sensory cues of depth are relative, such as which object obscures another and is therefore closer to the eyes. Accurate manipulation requires awareness of the absolute position in all directions. The main visual cues for absolute depth are stereo (reconstruction of distance from the differences between the views of the two eyes), and parallax (reconstruction of distance from the changes in view as the head, and thus each eye, moves). The system shown in FIG. 3 relies on an arrangement of a pair of cameras (or one camera with a split view) and optics, so that the views captured geometrically correspond to the views that would appear to eyes in the expected locations. This approach is a great improvement over previous systems but does have limitations. In particular, unless the optics move as the eyes move (which is not impossible, but creates substantial difficulty, and requires mechanical motion of parts), the approach presents two fixed views, making parallax impossible.

It is an object of the invention to provide an imaging system and method which avoids or mitigates the problems of known systems described above.

SUMMARY OF THE INVENTION

According to a first aspect of the invention, there is provided an imaging system comprising: image capture apparatus for capturing an image of an operator work site, the image including depth information; and display apparatus in communication with the image capture apparatus, the display apparatus comprising at least one display screen and being arranged to receive the image captured by the image capture apparatus, including the depth information, and display to the operator the image captured by the image capture apparatus, including the depth information, on the display screen; wherein the display screen is located between the operator's eyes and the position of the work site.

The combination of the image of the work site which includes depth information together with the location of the display screen between the work site position, which is preferably below the display screen, and the operator's eyes, which are preferably above the display screen allows the return of a parallax depth cue. This cue is obtained without the need for mechanical motion of parts, because the computation of depth information may be handled in software. Such a depth cue has been absent from any enlargement system more powerful and complex than a single large lens. Provision of such a parallax depth cue allows an operator to accurately position tools in the depth direction of the work site, even without strong stereo depth perception. This enlarges the range of operators for whom the system is natural and usable with minimal training. Such advantages over eyepiece microscopes as the reduction of strain, since the operator is not compelled to keep head and shoulders in a fixed position throughout any procedure, become even stronger in the presence of parallax, since the apparent position of the work site is more stable than with stereo alone.

The imaging system may be referred to as a flatscope in this specification. The position of the work site may be the actual physical location of the work site if the operator is working directly on the work site. Alternatively, if the operator is working on a remote work site via remotely controlled tools, the position of the work site may be the hand-sensed position of the work site as sensed by the operator as the operator controls the tools.

The at least one display screen may comprise a single display screen between the eyes of each of a plurality of operators and a shared work site. Alternatively, the at least one display screen may comprise a plurality of display screens, each display screen between the eyes of a respective operator of a plurality of operators and a shared work site. In a preferred embodiment, the plurality of display screens comprises two display screens.

In one embodiment, the image capture apparatus comprises a camera capable of obtaining depth information. Such a camera capable of obtaining depth information may be of the type described by K. Fife, A. El Gamal and H-S. P. Wong, in "*A 3 M Pixel Multi-Aperture Image Sensor with 0.7 μm Pixels in 0.11 μm CMOS*", IEEE ISSCC Digest of Technical Papers, pp. 48-49, February 2008, or of another suitable type.

In an alternative embodiment, the image capture apparatus comprises a plurality of cameras, and the depth information is obtained by comparing images captured by the plurality of cameras. In that case, depth may be determined by a variety of methods well known to those skilled in the art, including but not limited to computed stereo from two or more standard images, the use of structured light, or active devices depending on the timing of a reflected signal, such as ranging by laser or ultrasound devices.

Alternatively, the image capture apparatus may comprise a plurality of cameras and the depth information may be implicit in the images obtained by the plurality of cameras. Then, comparison of the images gathered by the plurality of cameras may occur in the visual system of the human operator.

The at least one camera and the display screen may be provided in a hand-held device, for example a Personal Digital Assistant (PDA) or cameraphone.

The depth information may be conveyed to the operator by management of the views delivered to each of the operator's eyes. The depth information included in the image may comprise information allowing the operator to determine depth by a stereo depth cue.

Preferably, the imaging system has real-time information of the position of one or both of the operator's eyes. The real-time information specifying the position of one or both of the operator's eyes may be data specifying the operator's head position. The depth information included in the image may comprise information allowing the operator to determine depth by a parallax depth cue. Preferably, such a parallax depth cue is provided from the changing view as the operator's eyes move, as determined by the real-time information of the operator eye position.

The real-time information specifying the position of one or both of the operator's eyes may be obtained by a tracking device worn by the operator.

The real-time information specifying the position of one or both of the operator's eyes may be obtained by one or more cameras mounted on the imaging system. The data obtained by the cameras may be analyzed to locate the positions of the operator's eyes.

The real-time information specifying the position of one or both of the operator's eyes may be used to control zoom of all or part of the displayed image. Eye-controlled zoom will be discussed further below.

Preferably, the depth information is conveyed to the operator by parallax as the operator's head moves. Thus, as the operator's head moves, the changing view corresponding to the new head position, allows the return of a parallax depth cue.

The image to be displayed for a particular eye may be selected from a plurality of camera images. Alternatively, the image to be displayed for a particular eye may be constructed by the use of depth data to adjust the image from a single camera. The image to be displayed for a particular eye may be selected to be the output of a single camera selected from a plurality of differently positioned cameras. The image to be displayed for a particular eye may be synthesized by interpolation between the outputs of two or more cameras selected from a plurality of differently positioned cameras. The image to be displayed for a particular eye may be synthesized from a three-dimensional surface model derived from the output of two or more cameras selected from a plurality of differently positioned cameras.

In one embodiment, the image capture apparatus comprises sensors for obtaining the image by detecting light in or in and around the visible range. The image may be sensed in three or more overlapping frequency bands. The three frequency bands may correspond to frequency ranges which stimulate red, green and blue receptors in the human retina. This may be achieved by extending into the infra-red range (for example as disclosed in US 2006/0097176 or US 2008/0260225) or by extending into the ultra-violet range or by subdividing the visible spectrum more finely.

In one embodiment, the image capture apparatus comprises sensors for obtaining the image by detecting radiated or transmitted infrared radiation.

In one embodiment, the image capture apparatus comprises ultrasound emitters and sensors. In that case, the display apparatus may be enabled to display the image on the display screen, such that the work site appears to the operator to be at a location substantially corresponding to the position of the work site. As already mentioned, the position of the work site may be the actual physical location of the work site if the operator is working directly on the work site. Alternatively, if the operator is working on a remote work site via remotely controlled tools, the position of the work site may be the hand-sensed position of the work site as sensed by the operator as the operator controls the tools.

The ultrasound emitters and sensors may be mounted on the display apparatus. Alternatively or additionally, the ultrasound emitters and sensors may be mounted on the work site. If the work site includes an operand, which is the subject of the operator's actions and the subject which is scanned by the ultrasound, the ultrasound emitters and sensors may be attached to the operand. If the ultrasound emitters and sensors are attached to the operand, the position of the ultrasound emitters and sensors may be tracked and added to the data received by the display apparatus, so that the real position of the scanned operand may be computed.

In one embodiment, the image capture apparatus is arranged to obtain the image by magnetic resonance imaging (MRI). Preferably, the image capture apparatus comprises a device for obtaining the MRI image, the device being magnetically and spatially compatible with the system.

In one embodiment, images obtained by at least two modes are combined to form the image displayed to the operator on the display screen, the two modes being from a set including but not limited to visible light, magnetic resonance, ultrasound and infrared radiation.

The display screen may be arranged to display supplemental images. In that case, the supplemental images may include annotations by automatic image analysis. Such automatic image analysis may integrate data from a plurality of modes including, but not limited to visible light, magnetic resonance, ultrasound and infrared radiation.

The display screen may be arranged to display supplemental images. The supplemental images may be displayed transparently, or inserted into the display, as desired by the operator. Those supplemental images are preferably images other than the current contents of the work site. The supplemental images may include recorded replays of the operator's actions, at standard or modified speed. The supplemental images may include data from records of the operand, the subject of the operator's actions. The supplemental images may include instructional material relevant to the operator's task.

The supplemental images may include annotations, for example from an external agent. Those annotations may report changes relative to measures computed earlier. Those annotations may report measures of properties of the subject of the operator's action. Those properties may include, but are not limited to, surface elasticity, necrosis, temperature, vascularization, inflammation, infection, perfusion, oedema, swelling, and gum retraction.

The supplemental images may include data from scans or images created at an earlier time. In that case, the scans or images created at an earlier time may be modified (for example, warped or otherwise changed in shape) to match the current shape of the subject of the operator's actions. Preferably, the supplemental images move in the display screen to retain the same apparent location as the subject of the operator's actions.

The supplemental images may include annotations by automatic image analysis. Such automatic image analysis may find distances, lengths, widths, or areas in the subject of the operator's actions. Such automatic image analysis may analyze surface shape of the subject of the operator's actions. Such automatic image analysis may analyze surface texture of the subject of the operator's actions. Such automatic image analysis may analyze colour in a plurality of frequency bands of the subject of the operator's actions. Such automatic image analysis may analyze temperature of the subject of the operator's actions. Such automatic image analysis may analyze a change in properties of the subject of the operator's action, over time. Such a change may be caused by the operator's actions. Such automatic image analysis may derive material or biomedical properties of the subject of the operator's actions. Such automatic image analysis may integrate data from a plurality of imaging modes. Such automatic image analysis may analyze any other desired properties of the subject of the operator's actions.

Data on the image may be made available to external communication systems. This may be for storage or for display or for other purposes. Preferably, this exchange adheres to industry standards for interoperability and data exchange.

In a preferred embodiment, detected positions of a tool or tools controlled by the operator or operators provide input to the imaging system. That is to say, the tools controlled by an operator may be used as input devices. The imaging system determines the tool position and uses that tool position to establish the desired input. Preferably, the detected positions of the tools are on the opposite side of the display screen from the operator's eyes, that is to say, in the vicinity of the work site. Thus, the operator does not need to move his hands substantially in order to control the imaging system, as well as to work on the subject in the work site.

The detected positions of the tools may be used to select modes of input. Alternatively or additionally, the detected positions of the tools may be used to select points or substructures in the displayed object. Alternatively or additionally, the detected positions of the tools may be used to mark annotations on the displayed object. Alternatively or additionally, the detected positions of the tools may be used to define spatial forms in the space of the displayed object. Alternatively or additionally, the open or closed state of the tool tip may provide input for the grasping or release of a virtual object. Alternatively or additionally, the motion of the tool tip or the state of the tool tip or both the motion and the state of the tool tip may be used to manipulate the shape of a virtual object.

According to a second aspect of the invention, there is provided a method for capturing and displaying an image of an operator work site, the method comprising the steps of: capturing the image of the operator work site, the image including depth information; communicating the captured image, including the depth information, to display apparatus comprising a display screen; and displaying to the operator the captured image, including the depth information, on the display screen located between the operator's eyes and the position of the work site.

The step of capturing the image preferably comprises obtaining the depth information by a camera capable of obtaining depth information. The depth information included in the image may comprise information allowing the operator to determine depth by a stereo depth cue. The depth information included in the image may comprise information allowing the operator to determine depth by a parallax depth cue.

Features described in relation to the first aspect of the invention may also be applicable to the second aspect of the invention, and features described in relation to the second aspect of the invention may also be applicable to the first aspect of the invention.

According to a third aspect of the invention, there is provided an imaging system comprising: a display screen for displaying an image to an operator; means to obtain real-time information specifying the position of one or both of the operator's eyes; and means to use changes in the position of the operator's eyes to control magnification of all or part of the displayed image.

That is to say, as the position of the operator's head and eyes changes, the magnification of the image displayed on the display screen changes. Preferably, as the operator's head and eyes move towards the display screen, the zoom (magnification) of the image increases so that the image is magnified and, as the operator's head and eyes move away from the display screen, the zoom (magnification) of the image decreases so that the image shrinks.

There is also provided an imaging system comprising: a display screen for displaying an image to an operator; means to obtain real-time information specifying the position of one or both of the operator's eyes; and means to use changes in the position of the operator's eyes to provide depth information to the operator.

The means to obtain real-time information specifying the position of one or both of the operator's eyes may comprise one or more cameras directed at the operator. The means to use changes in the position of the operator's eyes to control magnification of all or part of the displayed image may comprise a computer equipped with algorithms.

In one embodiment, the display screen shows images stereographically, by showing different images to each of the operator's eyes. In another embodiment, the display screen shows images with parallax, by adjusting the image according to the position of the operator's eyes. This may be adjusted separately according to the position of each eye, or adjusted based on a single position intermediate the two eyes.

The means to obtain real-time information specifying the position of one or both of the operator's eyes may additionally recognize steady gaze of the operator at a point on the display screen. Alternatively, further means may be provided to recognize steady gaze of the operator at a point on the display screen. If steady gaze of the operator can be recognized, the magnification of the image may keep fixed the point at which the gaze is steady. In that case, magnification of the image may be uniform throughout the image. Alternatively, magnification of the image may be greater in the vicinity of the point at which the gaze is steady than in the regions of the image further from the point at which the gaze is steady. The regions of the image further from the point at which the gaze is steady may move less or not at all.

The image may comprise a two-dimensional (planar) image and the magnification may apply to the two-dimensional image. Alternatively, the image may comprise a three-dimensional image, including depth information, and the magnification may apply to the three-dimensional image. In that case, if steady gaze of the operator at a fixed point can be recognized, the apparent depth of the fixed point relative to the display screen preferably remains fixed while the apparent sizes of the objects around the fixed point change.

Features described in relation to the first or second aspects of the invention may also be applicable to the third aspect of the invention, and features described in relation to the third aspect of the invention may also be applicable to the first and second aspects of the invention.

According to a fourth aspect of the invention, there is provided an imaging system comprising: motion capture apparatus for capturing motion of manipulated tools; and display apparatus in communication with the motion capture apparatus, the display apparatus comprising at least one display screen and being arranged to receive the motion data captured by the motion capture apparatus, and display to an operator the motion captured by the motion capture apparatus, in the form of images on the display screen; wherein the display apparatus is further arranged to display additional images on the display screen; and wherein the display screen is located between the operator's eyes and the position of an operator work site.

The combination of the motion data, which preferably comprises three-dimensional motion data, together with the location of the display screen between the operator work site position, which is preferably below the display screen, and the operator's eyes, which are preferably above the display screen, allows the return of a parallax depth cue.

The position of the operator work site may be the actual physical location of the operator work site if the operator is working directly on the work site. Alternatively, if the operator is working on a remote work site via remotely controlled tools, the position of the operator work site may be the hand-sensed position of the operator work site as sensed by the operator as the operator controls the tools.

The additional images displayed on the display screen may be images of virtual objects that can be manipulated by the operator. The additional images displayed on the display screen may be images of training materials, textual information, or a mentor. The scale relation between the captured motion and the displayed motion may be adjustable by the operator.

A mentor for the operator may operate another display and may be able to communicate with the operator by voice or video. The mentor for the operator may be able to impose motion on virtual tools active and visible on the display screen. The imaging system preferably reports visually and quantitatively the operator's success in matching the motion of the mentor's tools, recorded or controlled by current input from the mentor.

The display apparatus is preferably arranged to replay recorded events on the display screen. The operator may select that the replay of events is faster or slower than real time. In one embodiment, the additional images comprise images of a recorded procedure performed on real or virtual objects by another operator. The imaging system preferably reports how well the motions of the current operator conform to the motions of the recorded operator.

Features described in relation to the first, second or third aspects of the invention may also be applicable to the fourth aspect of the invention, and features described in relation to the fourth aspect of the invention may also be applicable to the first, second and third aspects of the invention.

According to a fifth aspect of the invention, there is provided an imaging system comprising: a hand-held device comprising a camera on a first side for capturing an image of an operator work site, the image including depth information, and a display screen on a second side opposite the first side, for displaying to the operator the image captured by the camera, including the depth information; and support means for positioning the hand-held device between the operator's eyes and the position of the work site.

The combination of the image of the work site which includes depth information together with the location of the hand-held device between the work site position, which is preferably below the hand-held device, and the operator's eyes, which are preferably above the hand-held device may allow the return of a parallax depth cue.

The hand-held device may be a cameraphone, smartphone, Personal Digital Assistant (PDA) or other portable device. The device preferably includes a software application which communicates to the display screen of the device an image of the operator's hands and any objects manipulated by them, at a size and focus depth controllable by the operator. The support means may be a stand for the hand-held device. The stand may be adjustable.

The position of the work site may be the actual physical location of the work site if the operator is working directly on the work site. Alternatively, if the operator is working on a remote work site via remotely controlled tools, the position of the work site may be the hand-sensed position of the work site as sensed by the operator as the operator controls the tools.

Preferably, the camera of the hand-held device comprises a camera capable of obtaining depth information. Such a camera capable of obtaining depth information may be of the type described by K. Fife, A. El Gamal and H-S. P. Wong, in "*A 3 M Pixel Multi-Aperture Image Sensor with 0.7 μm Pixels in 0.11 μm CMOS*", IEEE ISSCC Digest of Technical Papers, pp. 48-49, February 2008, or of another suitable type. The camera may be a video camera. The camera is preferably capable of being focused on the near field.

Preferably, the operator is able to control the sensitivity, dynamic range and spectral characteristics of the camera of the hand-held device by any suitable means. Alternatively or additionally, the operator may be able to control the manner in which camera data are represented in the display screen.

The hand-held device may also include a camera directed toward the operator. The camera directed toward the operator may be able to track eye movements of the operator. The tracked eye movements may provide control of the camera or hand-held device. The hand-held device may also a microphone directed toward the operator. Control of the camera or hand-held device may be by voice.

The hand-held device may also include also a network connection. This allows other persons (equipped with any connected display screen) to watch the same image as the operator. The person watching remotely may be able to control the view. The person watching remotely may be able to advise the operator, by voice or by image or by any other means.

The imaging system may allow the operator to choose spectral representation in the display screen that is particularly indicative of a particular state of the object being manipulated. For example, the particular state may be temperature, vascularization, inflammation, infection, perfusion, oedema, swelling or gum retraction. The particular state may be detected by algorithmic analysis and shown by colour coding.

Features described in relation to the first, second, third or fourth aspects of the invention may also be applicable to the fifth aspect of the invention, and features described in relation to the fifth aspect of the invention may also be applicable to the first, second, third or fourth aspects of the invention.

According to a sixth aspect of the invention, there is provided an imaging system comprising: image capture apparatus for capturing an image of a subject, for detecting light in or in and around the visible range, and classifying the captured light into more than three frequency bands; and computing means for determining from the captured image, the spectral reflectivities of the subject and the lighting conditions when the image was captured, and for producing a further image, in the more than three frequency bands, of the subject in user-specified lighting conditions.

Preferably, the computing means comprises means for transferring captured image data to a permanent store. Preferably, the computing means comprises means for attaching a captured image to a time series of images of the same subject, by means of date and identity.

The computing means may produce the further image with the aid of including in the captured images a standard object whose reflectivity is known for all of the more than three frequency bands. The more than three frequency bands include the near infrared. The more than three frequency bands include more than one band within each of the standard sensitivity bands, red, green and blue, of the human optical system.

The computing means may match the multi-spectral reflectivity of a region of a captured image, as computed by the imaging system, to a mixture of materials with known reflectivity. That mixture of materials will closely reproduce, under many lighting conditions, the colours observed by the human optical system when observing the material corresponding to that region of the image.

Features described in relation to the first, second, third, fourth or fifth aspects of the invention may also be applicable to the sixth aspect of the invention, and features described in relation to the sixth aspect of the invention may also be applicable to the first, second, third, fourth or fifth aspects of the invention.

BRIEF DESCRIPTION OF THE DRAWINGS

Existing systems have already been described with reference to the accompanying FIGS. 1 to 5, of which:

Embodiments of the invention will now be described, by way of example only, with reference to the accompanying FIGS. 6 to 8, of which:

FIG. 7a is an underside view of a display screen for use with an imaging system such as that of FIG. 6a;

FIG. 7b is an elevation view of the display screen of FIG. 7a; and

DETAILED DESCRIPTION OF PREFERRED EMBODIMENTS

In the prior art system shown in FIG. 3, the long-barrelled cameras, whose geometry was described as compensated by mirrors, can now be replaced by cameras flat enough to be placed directly under the display screen 303, facing the work site. An example of such a thin system which enables "a 3D depth map without the need for active illumination or calibration" is described by K. Fife, A. El Gamal and H-S. P. Wong, in "*A 3 M Pixel Multi-Aperture Image Sensor with 0.7 µm Pixels in 0.11 µm CMOS*", IEEE ISSCC Digest of Technical Papers, pp. 48-49, February 2008, the details of which are hereby incorporated by reference. The small differences between the light captured by the different apertures in that device allow computation of depth data. This is analogous to the use of greater differences in the views by physically separate eyes or cameras. After the depth computation, each pixel of the processed image has a depth associated with it. This illustrates that images with depth data can be captured from a single device, with a size and fabrication technology which make consumer products realistic, and this capability in image sensing devices may be incorporated into an imaging system such as a flatscope. Alternatively, depth may be determined by a variety of methods well known to those skilled in the art, including but not limited to computed stereo from two or more standard images, the use of structured light, or active devices depending on the timing of a reflected signal, such as ranging by laser or ultrasound devices.

Figure 6A:
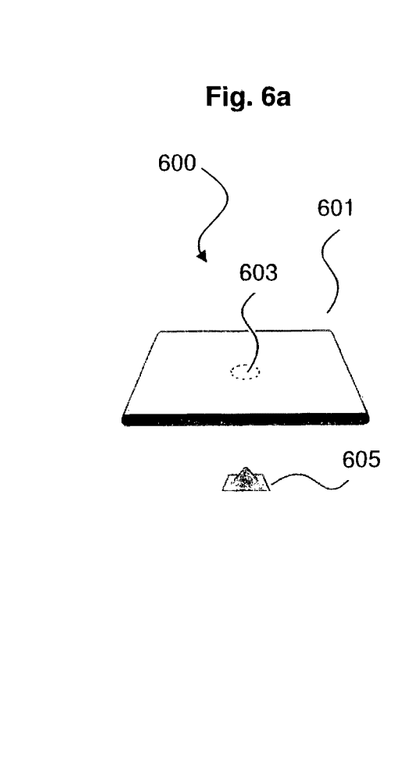
FIG. 6a shows an imaging system according to one embodiment of the invention.

FIGS. 6a to 6d show an embodiment of an imaging system or flatscope 600 according to the invention. FIG. 6a shows a display screen 601 including a single depth-reporting camera 603 centred on the underside of the display screen 601. (The depth-reporting camera 603 may be of the type described by K. Fife, A. El Gamal and H-S. P. Wong, in "*A 3 M Pixel Multi-Aperture Image Sensor with 0.7 µm Pixels in 0.11 µm CMOS*", IEEE ISSCC Digest of Technical Papers, pp. 48-49, February 2008, already discussed, or of another suitable type.) The camera 603 may alternatively be provided at another location on the underside of the display screen, or multiple cameras may be used, as will be described with reference to FIG. 7. Below the display screen is an operand 605, which an operator wishes to see in magnified view.

Figure 6B:
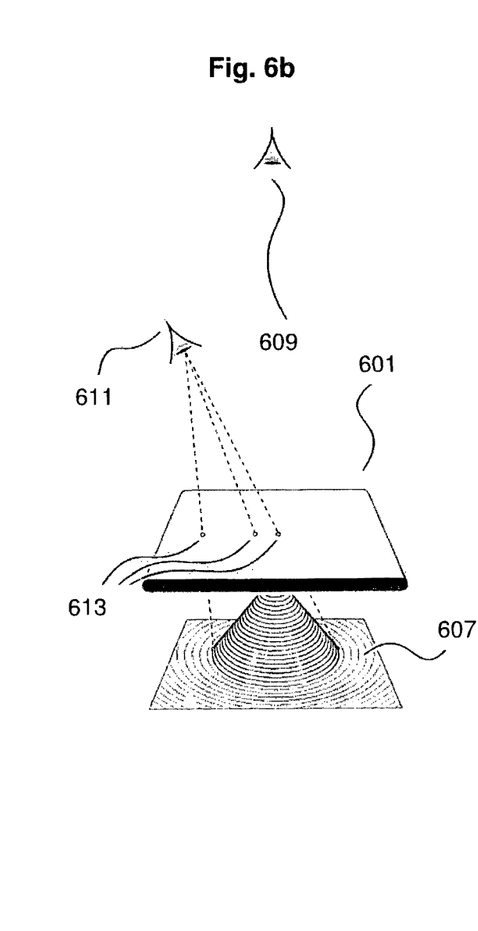
FIG. 6b shows the imaging system according to FIG. 6a, with two alternative operator positions.

FIG. 6b shows the display screen 601 and the operand seen as a larger object 607, by means of appropriate imaging, on the upper surface of the display screen 601. The operator's eye or eyes (seen in profile in FIG. 6b) may be located at position 609 which is vertically centred above the display screen 601. Alternatively, the operator's eye or eyes may be located at position 611 which is angled from the vertical and off-centre.

Figure 6C:
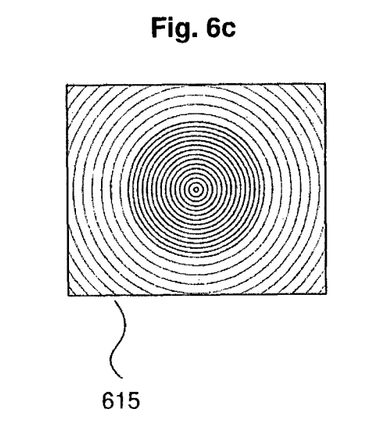
FIG. 6c shows the display with the first operator position of FIG. 6b.

FIG. 6c shows the view 615 from the camera 603, with the operator's eye or eyes located at position 609 which is vertically centred above the display screen 601. The view 615 is approximately correct for the intended apparent size and location of the virtual operand 607.

Figure 6D:
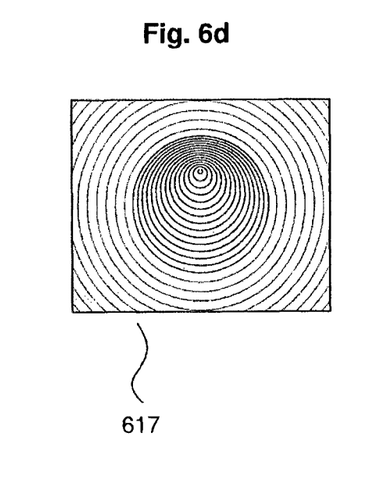
FIG. 6d shows the display with the second operator position of FIG. 6b.

FIG. 6d shows the view 617 from the camera 603, with the operator's eye or eyes located at position 611. When the operator's eye or eyes are in location 611, three points equally horizontally spaced on the virtual object 607 should be rendered at the points 613, on the direct lines between the points on the enlarged operand 607 and the eye location 611. This correctly locates their images, as seen from the position 611. Due to the unequal separations between those points, the optimal image to be rendered on the display screen is as illustrated in the view 617. This view may straightforwardly be produced by computational methods well known to those skilled in the art, provided the depth information is available. Using pixel coordinates (i,j) for the display, with the current digital magnification, colour and depth data are provided at spatial co-ordinates (i,j,d(i,j)), showing a view of the visible surface from a specified point for an eye or virtual camera.

Alternatively, a tracking device may be fitted to and move with the operator's head, to provide the eye-position data. If the user is wearing shutter glasses, or other support for stereo display, the tracking device may be attached to or embedded in the structure of the glasses. It is important that sufficient computing resources be available to deliver the image depth and eye location data accurately in a short time, preferably substantially shorter than the refresh interval of the display screen, which is typically of the order of 20 ms. This is so that the refreshed image is redrawn using appropriate data. If the image shown changes correctly with head motion, as sensed by the operator's inner ear, parallax provides a strong sense of a stably located operand 607 at a well-defined position, even in the absence of the stereo depth cue, which for some operators is always absent or weak in any case. Inaccurate or out-of-date eye locations make the object appear to jitter in space, and this can produce results less useful than a simple display of the untransformed view from a camera at the location 603.

Tracking data should be available to the processes described below with a latency below approximately 20 ms. Latency is defined as the time between the device being physically in a location and the time that location is delivered to the rest of the system. Latency is not, as often defined by tracking device manufacturers, the time to respond to a query with the most recent position computed, at an unspecified physical time. In both cases, prediction based on recent data may be used to improve the estimate of eye position at the time of the next refresh of the screen. That estimate is used in preference to recent positions directly measured or computed. The appropriate view 617 may be rendered fast as a "terrain" by methods well known to those skilled in the art, without the need to construct a mesh of triangles on the fly for standard general surface rendering.

Figure 7A:
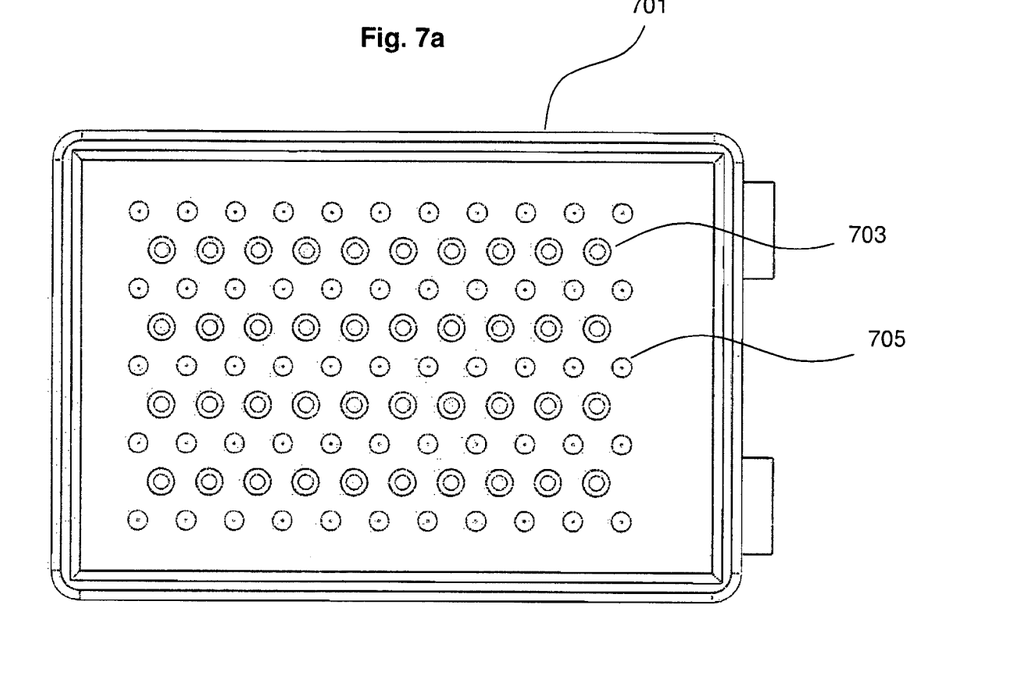
Figure 7B:
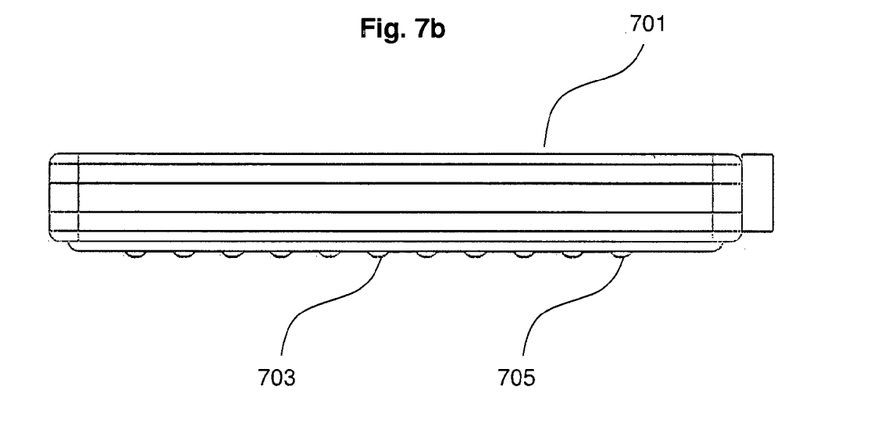

FIGS. 7a and 7b are more detailed views of a display screen for use with an imaging system like that shown in FIGS. 6a to 6d. FIG. 7a is an underside view of a display screen 701 and FIG. 7b is an elevation view of display screen 701. Under the display screen 701, one or more camera units 703, and one or more lights 705 are provided. FIGS. 7a and 7b show a plurality of camera units and lights, but any arrangement that provides shadow-free lighting and depth data is within the scope of the present invention. As previously discussed, even a single multi-aperture chip can now provide depth data, but wafer-level optics has reduced the size and price of visual sensors to the point where minor advantages can justify their use. If two cameras are used, their images may be computationally compared so as to derive depth data. This may be provided as an alternative to, or to enhance the precision of, single-camera depth reporting. Alternatively, the two cameras may simply be arranged as a pair of stereo views reaching the operator's eyes (although this is not preferred). An operator with good stereo depth perception then acquires a clear sense of the depth of different parts of the displayed region, appropriately magnified if the angular separation of the camera positions is appropriate. However, explicit depth data is required for a parallax depth cue.

One or more video cameras, whose field of view includes the expected range of positions of the eyes of the operator or operators, may be provided. The output of the camera or cameras is transmitted to a digital processor, which identifies the positions of the operator's eyes within the images. Various means of doing this are well known to those skilled in the art. If there is a plurality of cameras, triangulation then establishes the three-dimensional location in space of the eyes relative to the display screen. If only one camera is provided, that camera is able to capture depth, so that, again, the three-dimensional location of the eyes becomes available. If more than two cameras are installed, or a plurality of cameras with depth reporting is provided, the redundancy may be used to improve the accuracy of the position data for the eyes.

An advantage of using multiple cameras is that fewer points hidden from a camera location such as 603, but visible from an oblique eye position such as 611, must be rendered by interpolation (computational guessing). Every point visible to the operator through the display screen 601 is visible to a camera at some location under the display screen. There is some added complexity to the depth data structure, and consequently to the rendering algorithms, since a sideways view can include points overhung by others, but many ways of dealing with this added complexity will be evident to those skilled in the art. All the processes discussed above, whether in determining depth and eye data or in rendering, are extremely compatible with parallel computing methods that fit well in the pipeline of graphics processing units (GPUs) with hundreds of parallel cores, that can now be programmed directly using programming language extensions such as CUDA (Compute Universal Device Architecture).

In an alternative embodiment, where the imaging system uses multiple cameras and the direction of view from the current position of the eye or eyes is intermediate between the directions in which two or more cameras view the work site, interpolation between the views reported by those cameras gives an image in the appropriate direction, by planar image manipulation methods. However, this does not take into account the changing distance of an eye from the display, and thus cannot present an apparent operand 607 as stable as the use described above of explicit depth data.

Referring to the imaging system described with reference to FIGS. 6 and 7, eye-position data may be used for control of the system by the user in various ways, as described above. However, an important feature is that the combination of depth data for the image of material below the display screen and location for the eyes above it, permits the return of the parallax depth cue which, until now, has been absent from any enlargement system more complex and powerful than a simple lens. The depth data, taken together with the increased speed and reduced cost of computation, allows the addition of the parallax depth cue to a flatscope, enlarging the range of operators for whom the system is natural and usable with minimal training. Such advantages over eyepiece microscopes as the reduction of strain, since the operator is not compelled to keep head and shoulders in a fixed position throughout any procedure, become even stronger in the presence of parallax, since the apparent position of the operand is more stable than with stereo alone.

The image may be obtained by sensors detecting light in or in and around the visible range, for example the visible spectrum, plus the near infra-red and/or the near ultra-violet. The image may be sensed in three or more overlapping frequency bands and these may roughly correspond to ranges which stimulate red, green and blue receptors in the human retina. This may be by extending into the infra-red range, for example as disclosed in US 2006/0097176 in the name of Szu or US 2008/0260225 in the name of Szu. The image may be obtained by sensors for detecting radiated or transmitted infrared radiation. Alternatively or additionally, this may be by extending into the ultra-violet range or subdividing the visible spectrum more finely. Such image sensing techniques have become practical at an economic and technical level appropriate for wide use in medicine and other fields. However, image sensing using light in or in and around the visible spectrum is only one of the modes by which an image, including depth data, may be generated for display on the display screen of the imaging system. Any real-time image acquisition system may be used, including but not limited to the arrangements in the following paragraphs.

An ultrasound signal may be emitted by one or more emitters attached to or embedded in the imaging system. Alternatively, the emitter or emitters may be located against part of an object that is under the display, such as a human or an animal, optionally with gel or other means to reduce impedance between the emitter and the object. Sensors for echoed sound are placed similarly, and may or may not be part of the same device or devices. In the case of sensors and emitters moved separately by the operator or moving with the operand, the emitters and sensors may be tracked in real time, for example by analyzing the images from the camera unit or units 703, or by other means known to those skilled in the art. Thus, each element of the ultrasound-derived three-dimensional image has a known location relative to the display screen. The display screen is thus enabled to display the ultrasound-derived image in a stable view, with hand-eye co-location, using any convenient magnification factor. In a preferred embodiment, the ultrasound-derived image is combined (fused) with a visual image, so that if the operand is a patient the effect may be of a view through translucent skin. This embodiment is particularly useful for minimal access procedures, where the operator inserts small tools through holes in the skin, rather than creates a large opening for a direct view. Examples include, but are not limited to, biopsy, laparoscopy and arthroscopy.

In many prior art systems that use ultrasound, the operator must look at a display in a location far from the operand, and possibly rotated relative to it. For example, an ultrasound display screen is often placed to one side of the operator, with a view whose orientation varies with the hand holding the device. For example, a laparoscopy display in front of a surgeon may show the view from a movable camera inside the abdomen, a distance below the screen, and including indirectly controlled tools. The resulting difficulty of hand-eye coordination increases error rates, strain on the operator, time to complete a procedure, and cost. Providing the ultrasound-derived image on the display screen 601 between the operator's eyes and the operand 607 may reduce this difficulty. In many cases, the present embodiment of the invention can replace the inserted camera as an imaging means, reducing the invasiveness of a procedure.

An imaging system constructed of magnetic resonance imaging (MRI)-compatible material (without electromagnetic effects that interfere with MRI, and not harmed by the large magnetic fields used), used in an open MRI system, allows an operator hand-eye co-located manipulation of an operand imaged using magnetic resonance. Similarly, nuclear medicine imaging, such as positron emission tomography (PET) may be incorporated into the imaging system. As with ultrasound, in a preferred embodiment, the MRI-derived or PET-derived image is combined with a visual image.

Continuous or frequent exposure to X-rays, and thus to computerized tomography (CT), is unwise, but interventional radiography uses X-ray snapshots to guide catheters and other minimal access tools. Often, an injected contrast agent makes arteries or other structures visible. Views from two directions (as in stereo vision) can produce a three-dimensional map for three-dimensional location. Similarly, ultraviolet imaging may be incorporated into the imaging system. If this is combined with a visible display in a flatscope, the operator's manipulation becomes easier. If the patient or other operand moves or is moved during a procedure, the displayed position becomes outdated. An embodiment of the present invention uses the geometric data from the cameras to construct a model of the bending and motion of the operand, and uses this to update the displayed X-ray data. More generally, such geometric update data may be applied to recent data acquired in situ, from X-ray, MRI, PET or any other scanning method, and adjusted to the geometry revealed by the visual component of the imaging system.

The image displayed on the display screen may also be derived from simulation, where a good enough interactive model of the operand is available. The image displayed on the display screen may also be derived from a recording of an earlier procedure or an earlier part of the current procedure. The recording may be played back at the original speed, or faster, or slower. This may be used to watch a procedure or a step in more detail, to analyze the errors of an individual operator, or for emulatory training. The current operator's tools may be added to the view of a procedure performed earlier by an expert, and (optionally starting with a slowed version), the current operator may attempt to reproduce the motions of the expert. The system measures and reports on the success of this attempt. Simulation and recording are discussed more fully below.

The image displayed on the display screen may also be derived from a remote site, where a camera scheme compatible with that of the imaging system exists at a remote location. It is preferable that this is another flatscope, but the imaging system can accept image and annotation information in widely used formats such as DICOM, and thus support information from any remote site that implements industry standards. Similarly, the images and annotation collected by the imagine system of the invention and constructed by an operator may be exportable in real time to any standards-compliant device. If remotely controlled tools are available at a site which is thus receiving an image of the operand and transmitting responses, the remote operator can then act directly upon the operand. If they are not, the remote operator's local tools can be used for pointing, annotation and so forth, creating signals that add transiently or otherwise to the view seen by the operator on the spot. This may be used for mentoring and consultation. Note that if an operator works on a remote site via remotely controlled tools, for example, the location below the display screen is the position of the operand as sensed by the operator, not the physical location of the operand itself.

As discussed further below, for a flatscope, user input is often better with the operator's hands below the display, rather than above the display (as with a touch-screen) or to one side of the display (as with a mouse). One reason to avoid screen-touching during a procedure is that a surgical or other physical operand is a rich source of material which could reduce visibility. Any visible smear on the display screen may be a serious problem. It is preferable, therefore, that screen touching is reserved for initial tasks of setup and calibration.

Unlike the planar input of any screen-oriented interaction, whether an object or cursor is moved co-locationally by tracking touch, or indirectly by a mouse or other device, the imaging system may have co-locational tools as part of its design. The operator is familiar with delicate use of these tools to act on a physical operand, and it is natural to extend them to control of the imaging system. The operator's hands need not change to a different control object, nor to a different space such as a mouse-pad or the front of a screen. The tip of a scalpel, forceps, engraving tool or other implement held by an operator moves with the usual degrees of freedom: translation back and forth, side to side, up and down, and rotation about any axis, including the forward, lateral and vertical axes. The human operator is accustomed to manipulating these degrees of freedom simultaneously.

To use these tools or tool tips as input devices, it is necessary for the imaging system to have explicit data specifying (or to "know") their positions. Various tracking devices well known to those skilled in the art may be attached to such tools. These include, but are not limited to, a robot arm, a receiver of radio-frequency signals or ultrasound from a fixed emitter, and light emitting diodes or other point sources of light to be detected by a camera, and any of these may be used within the scope of the present invention. It is preferable, however, that any pointed rigid object entering the field of view of the camera or cameras of FIGS. 7a and 7b may serve as an input device, without special attachments. Computer vision does not yet match the human brain in general object identification in arbitrary scenes. However, finding rigid objects of a known shape (for example, one tool shape in a tool shape database used in a particular field of imaging system use), in front of a scene rather than partly obscured, and with controlled lighting, is a task for which many solutions are known to those skilled in the art. Thus, such positional information can be assumed to be available, in real time, to the imaging system. The imaging system can therefore determine the location of the tool or tool tip, the location on the operand to which the tool or tool tip is pointing, the location on the operand which is closest to the tool or tool tip, the locations on the operand within the current active radius of the tool or tool tip, the locations on the operand within the simulated airbrush effect region of the tool or tool tip, the gesture the tool or tool tip is making (where the gesture may be a learnable motions such as moving the tool tip in a small circle) and other such locations or movements. The imaging system can then base actions upon these determinations.

A tool may be used in "physical only" mode, in which its effects are only those resulting from physical interaction with the operand, such as cutting, cauterizing, and grasping. Alternatively, the tool may be used in other modes, such as selection mode, painting mode, and false-coloring mode. The operator may cause the tool to enter or leave a mode by voice interaction, for example speaking a predetermined word or phrase into a microphone connected to the imaging system, by placing the tool tip in a menu region of the display screen, by making a recognized gesture with the tool tip when the tool tip is visible at a distance from the operand, pressing a foot button, or by other means that will be evident to those skilled in the art. One or more buttons may be added to the hand-proximal part of a tool in order to move the tool between modes. However, it is preferable that the tool may be used without redesign or additions. In that case, addition of a new tool requires only the inclusion of its tool shape in the tool shape database. That shape may be imported from its manufacturing computer-aided design (CAD) specification, or from a three-dimensional scan of an example of the tool, by means well known to those skilled in the art. The effect of any of these mode changing actions may depend on context.

Certain tools, including needle holders, forceps, tweezers, scissors, biopsy needles with active capture at the tip, and many other devices, have visually recognizable states of being "open" or "closed" at a distal end. The open or closed state is under the control of the operator, typically by relative motion within the operator's grip. Recognition of these states permits a further class of control mechanism, including a three-dimensional version of the familiar computer-mouse "drag and drop" mechanism. The operator may close the tip at or near a particular element or location on the image, and may move or extend that element or a new element to the three-dimensional location where the tip is open. This may be used for simple transfer, for example of a tag indicating the next point for cauterization, or for "rubber banding" which creates a line starting point where the tip closes, and an end point for that line where the tip next opens. For curved visible paths, a "grab by closing, drag, release by opening" mode may allow the operator to change the shape of the path. The typical curve-dragging familiar to computer mouse users moves an interpolation or control point (x,y) to a new point (x',y') without direct control of the direction of the path. However, the six degree-of-freedom input natural to a tool in the imaging system according to this embodiment of the invention allows the operator to move the tool tip from a point (x,y,z) to a new point (x',y',z'). A path control can move with it simultaneously. And, the operator can turn the tool tip while moving, so that the direction of the path through the point turns similarly. Fewer motions are thus needed to specify a complicated path, such as instructions by a mentor to a trainee or robot as to the safe way another tool should move.

If the operator signals (by a voice command, gesture, menu choice, or other means known to those skilled in the art) that the tip of the currently held tool is to become an annotator, it may become a brush, pencil, curve creation tool, or other marking widget as familiar in applications such as Adobe PhotoShop™. However, in such applications such widgets create a set of colour values associated with pixels in a planar image, but in the flatscope, the data created may include depth values, controlled by the positions of the tip as the creation take place, and become associated with the imaging system's internal representation 607 of the operand 605. Alternatively or additionally to colour markings, the values may include tags such as labels for particular points or substructures of the operand, and classifications (for example, "necrotic" or "not to be cut"), which may be displayed by modifying the colour in which a set of pixels is displayed, but are not to be identified with colour values. Among other consequences of this difference, the system can permit the operator to choose to show certain (for example, necrotic) points as darkened, lightened, blue, and so on, as desired. In a preferred embodiment the marking mode is set by the user, attaching values either to particular points on the surface of the operand, or to particular points in the work site. If values are attached to particular points on the surface of the operand, the marking may be of the points behind the tip relative to the operator's current viewpoint, of the points nearest the tip, of the points reached by a virtual airbrush, or of points selected by other criteria. If values are attached to particular points in the work site, the operator may create free-form structures in space, which are displayed as obscuring the operand 607, opaquely or translucently, or being obscured by the operand, according to the needs of a particular application. In a preferred embodiment, all such display is adjusted to the point of view of the operator, as shown in FIG. 6b.

As already discussed, the system may create a deformable model of the operand, which adjusts its position to match the current image data. If the operator modifies (for example, cuts) the operand, the model must change topology as well as deform. In the preferred embodiment, the annotations of points on or in the operand move with the locations of points in such a model, so as to appear as though painted or drawn on the operand itself, as seen through the display screen.

Many important annotations are semi-automatic, in that the operator sets the purpose and scope, but the assignment of annotation range to particular parts of the operand is computational. For example, the user may select a point (means of selection have already been discussed) and by voice, menu, gesture or otherwise, request the system to identify the structure (for example, tube, artery, lesion), of which the point is a part. The system then highlights the identified structure. If the identified structure is larger or smaller than the desired object, the operator may request "larger" or "smaller" by voice, identify the kind of structure sought (for example, by saying "tube"), use detailed editing tools to change the displayed boundary, or use any other suitable technique to change the selected structure. The operator may request the computation of various parameters of the structure, for example, the area, length, diameter, thickness, rugosity (rough or smooth), degree of inflammation and estimated blood flow, according to the particular analysis capabilities. Among the desired capabilities for medical applications is the identification and quantification of oedema (fluid swellings). Where a swelling visibly interrupts the apparent shape of a tissue, a surface may be computationally fitted according to the originally shaped tissue (for example by combining measures of bending and of distance from the unaffected region). This gives a reference surface against which the volume of swelling (the region between the interpolated and actual surfaces) can be quantified.

As already noted, it is increasingly possible and economic to acquire images with more spectral information than the standard set of three colour bands, red green and blue. Just as visible colour allows discrimination beyond what is possible in a grey scale image, increased spectral range and refinement enable machine recognition of material properties not apparent to the naked eye. For example, the temperature or the spectral characteristics of a particular type of infection with a large yield of, for example, a molecule highly reflective in specific frequency sub-bands, for example, red or blue, may be recognized. Other phenomena such as a bruise may give the same sense to a human eye, by stimulating the red and blue frequency bands to the same total extent, but may be easily distinguished by the system because of the reflectivity in sub-bands. An application-specific imaging system such as one intended for microsurgery, may include in its programming the signatures of a wide range of relevant phenomena. In this way, the operator can call on the system to identify one of the phenomena and mark (for example, in human-visible pseudo-colour) the region in which it is present. In a preferred embodiment, a background routine automatically checks for the spectral characteristics of a predetermined checklist of properties that are clinically or otherwise important in the particular application, and alerts the operator to their presence. With cameras sensitive in the infra-red, the system can also deduce temperature, and derive measures of inflammation from this and other spectral contrasts with surrounding tissue. Upon operator request, these measures may be overlaid either on the entire surface by a graphic device such as false colour or contours, or only upon the region where abnormal values appear. Other imaging modalities such as ultrasound make it possible to derive physical quantities such as surface elasticity, which may also be added as visible annotations.

A frequent action by microsurgeons is to press upon an artery and observe the change of colour with time after blockage of the blood flow. The red colour is lost and blood that does not drain turns blue, indicating the strength of drainage. The artery may then be released and the change of colour with time to return to the previous state may be observed. Similar actions may occur in any field in which the operator acts on an object with its own internal dynamic. In most cases, like the blood flow example, this observation is currently unquantified, but the imaging system may be instructed to observe and record the events, optionally attaching the data to a tag. Automatic multi-spectral analysis maps the region that changes and estimates, for each part of it, the degree to which it is influenced. In the blood supply case, this marks to what extent each part of the tissue depends on the specific artery branch that is blocked. Most points in tissue have at least some redundancy in supply. Material or biomedical properties derived from these measures may also be added as visible annotations.

From one or more of the above measures, the system can detect or quantify features or parameters significant to the operator. These may include, but are not limited to, skin elasticity, necrosis, vascularization, infection, perfusion, oedema, swelling, or gum retraction in medical uses, remaining water content in clay for a sculptor, and other quantities familiar to those skilled in an art in which the imaging system may be used. In a preferred embodiment, those quantities are shown as annotations visually attached to the operand 607, visible in the display screen at the same structural point through all motions and changes in viewpoint.

Figure 8:
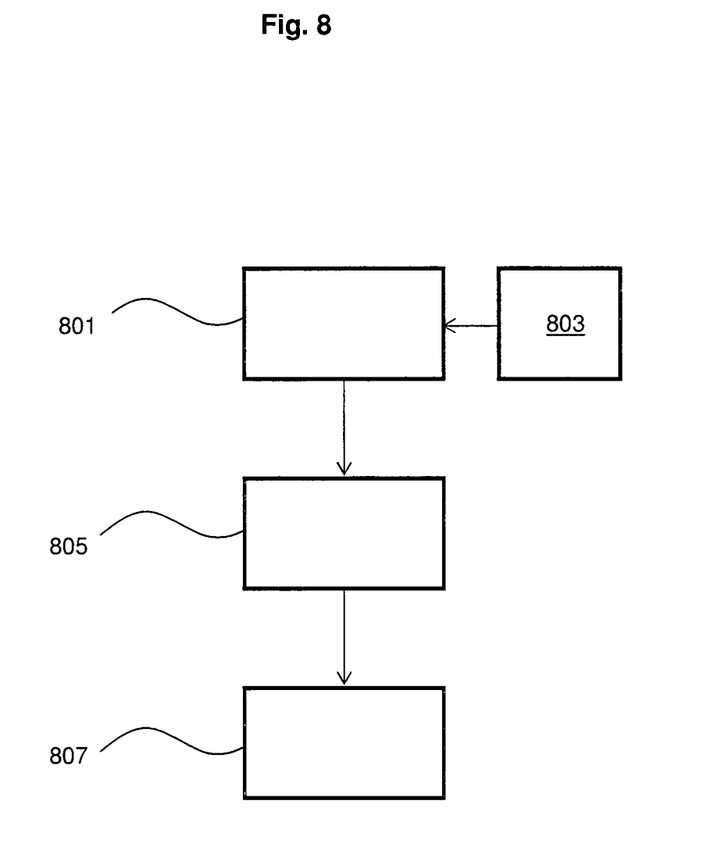
FIG. 8 is a flow chart showing the steps performed by an imaging system according to one embodiment of the invention.

FIG. 8 is a flow chart showing the steps performed by the imaging system according to one embodiment of the invention. The imaging system or flatscope may have the form shown in FIGS. 6a and 6b. In first step 801 an image of an operand at an operator work site is captured. Examples of such an image are shown in FIGS. 6c and 6d. The image includes depth information 803 which, as already discussed, may be obtained from one camera capable of obtaining depth information, or multiple cameras. In second step 805, the image is communicated to display apparatus, such as display screen 601 in FIGS. 6a and 6b. The display screen is located between the operator's eyes (for example at position 609 or position 611) and the operand and operator work site. In third step 807 the image, including the depth information is displayed on the display screen. An important feature is that the combination of depth data for the image of material below the display screen and location for the eyes above it, permits the return of the parallax depth cue.

As well as the hand and voice controls already described, it is preferable that the imaging system be controllable by the position of the operator's head and eyes. As already discussed, the position of the operator's head and eyes may be used to display images with appropriate parallax, perspective and stereo depth cues, for a display object 607 (see FIG. 6b) with a given virtual position. It follows that, if the operator's head approaches the display screen, the object 607 will take up more of the operator's field of view. However, if only this mechanism applies, the object 607 does not appear to be larger. The human vision system adjusts to see the object as close, but with the same size. Instead, here the movement of the operator's head is used to change the perceived size.

With zoom mode turned on (for example by voice, by a foot pedal, by a menu choice or by other suitable means), the eyes' approach to the display screen results in a spatial enlargement of the display object 607. Thus, the display object 607 appears larger, for examination in greater detail. Similarly, moving the eyes away from the display screen reverses the effect. The factor by which movement translates into an enlargement ratio $\lambda$ may be set by default. For example, an approach of a=7 cm may produce a doubling of apparent size by virtue of $\lambda=2^{a/7}$. The enlargement ratio may be modifiable by operator preferences. The default enlargement ratio may be reached by study of a representative group of operators, by a consensus procedure or by any other suitable method.

The simplest implementation of such a zoom process replaces each display location (x,y,z) of a point in the operand or on a tool by ($\lambda$x,$\lambda$y,$\lambda$z). This always transforms (0,0,0) to the point (0,0,0) and this point is fixed (for example at the centre of the displayed image). Other points move radially toward or away from that fixed point.

However, in the preferred embodiment, the fixed point is (X,Y,Z) which is under operator control and the formula becomes (x,y,z)→(X,Y,Z)+($\lambda$(x−X), $\lambda$(y−Y), $\lambda$(z−Z)). The operator may choose the point (X,Y,Z) by holding a tool tip there, or by fixing the gaze of the eyes on it or by other suitable means. (Means well known to those skilled in the art detect the direction in which eyes are looking, as well as the point from which they look, and compute either the point where the gazes of the two eyes meet, or the point where the gaze direction meets a displayed element of the operand 607 or a tool visible within it). This point chosen by the operator to become the centre of the magnified displayed image becomes (X,Y,Z) used above. Since this point does not move in any direction, an object centred there does not appear to move closer or further away, but does appear to grow or shrink.

The enlargement ratio λ may be a single number. For example the enlargement ratio λ may be controlled by a formula (such as $\lambda=2^{a/7}$ in the above example). This responds to the change in operator distance, but the enlargement is the same for each display position (x,y,z) that is zoomed. Alternatively, the enlargement ratio λ may monotonically diminish with distance, by a formula such as but not limited to $\lambda=2^{a/7}/(1+c((x-X)^2+y-Y)^2+(z-Z)^2))$, where c fixes the rate of diminution. This gives a localized zoom, in which the region around (X,Y,Z) swells, an intermediate zone is radially compressed, and remote points barely move. At the expense of some distortion, the zoomed region is still seen in the same larger context, and navigation is easier.

The use of a fixed or variable enlargement ratio λ in display is well known to those skilled in the art, but the enlargement ratio λ is usually controlled by a slider or other draggable element of the display or its surroundings. The use of head motion in order to modify the enlargement ratio λ, has not been adopted in the context of a three-dimensional display such as the flatscope or other imaging system for examining images with depth, or even in the context of a system for working with two-dimensional planar images (with depth z and Z terms omitted from the formulae above).

As already mentioned, the image displayed by the display screen may be derived from simulation or recording. Indeed, the images displayed in the display screen need not be of a current real operand. Instead, they may show a recorded procedure. In a preferred embodiment, such a recording stores not only what was shown on the display screen as a sequence of planar images adjusted to the original operator's position and preferences, but the full input stream from the camera or cameras, and other sources of input. Thus, although an operator studying such a record cannot modify what is done in the procedure, the operator can replay the recording fast or slow, look from different positions or with different zoom factors, modify the apparent lighting, and apply any other data interpretation or analysis subsystem available. This may be useful either to a trainee, studying a procedure performed by an expert, or to a mentor or adjudicator assessing skill or problems in performance by an original operator. More actively, the trainee can practise following the tool control of an expert, with both the original tools and the trainee's tools visible in the display screen. Replay speed, magnification factor, zoom and other variables may be set either by the trainee or by a trainer or the system, with repeated or successive procedures adjusted for increasing realism and difficulty. Since the magnification factor and speed affect the difficulty of achieving any particular motion with the tool tip, this gives a capability to work gradually toward the hardest version, improving results and reducing training time.

Given an adequate system for simulating an operand and its response to tools, such a virtual operand can be imported into or connected to a flatscope, allowing a trainee or practitioner to improve without risk to a physical patient or other entity. All the display and interaction elements in the present disclosure apply also in this case of virtual operation.

In either the replayed or virtual modality, the system can add teaching materials to the display, detect errors and report them to the trainee and optionally to a mentor or institutional records. With either a replayed or simulated procedure, a mentor can be connected from another station, remote or nearby, for the various interactions already discussed.

Much of the functionality already described can also be realized by extending the hardware and software of a consumer device, for example but not limited to a personal digital assistant (PDA) or cameraphone. This is providing that the camera included as part of the PDA, cameraphone or other device is capable of obtaining depth information (a feature which is expected to become common). Preferably, the device also has means for eye tracking, either incorporated into the device or provided by a supplementary system. If the means for eye tracking is provided by a supplementary system, the supplementary system is preferably supplied as an integral part of a support frame or other component. This allows the PDA, cameraphone or other device to serve the extended function. The voice input features already described require access to the audio data stream of the device's telephone function, which is typically available, and access to sufficient processing power to recognize key words in real-time, which will be available in some cases. If the device has built-in voice control, this may be used directly.

Preferably, a support frame for the device is provided (this may be the same or in addition to the support frame integrating the supplementary system for eye tracking). The support frame may rest on a work base and hold the PDA, cameraphone or other device at an adjustable position between the operator's eyes and the operand. This may be at a distance of between 5 cm and 10 cm from the operand, although the particular distance will depend on the particular operand and use, and distances outside this range are also envisaged. The camera included in the PDA, cameraphone or other device is focussed on the operand, and the resulting view appears on the display screen of the device. Usually, the display screen shows the operand larger than the original. If the PDA, cameraphone or other device, or the support frame, includes means for eye tracking, preferably the PDA, cameraphone or other device includes an application which causes the display screen to show parallax as already described in general for a flatscope. If the display screen of the PDA, cameraphone or other device includes a means to show images in stereo, it is preferable that there be separate adjustment of the left and right eye images to the actual positions of the left and right eyes.

It is normal for such PDAs, cameraphones and other devices to be network-ready and be able to use substantial bandwidth. In that case, the remote user and mentor functionality already described is also applicable to this embodiment of the invention. The key differences are physical scale (the work site and display screen are smaller, and the available magnification may be less), and control of lighting. Other features such as multispectral imaging can be expected on some devices in this class, but not all. This may limit some functionality such as annotation.

Some PDAs, cameraphones and other devices will have sufficient processing power and adaptability to support flatscope functionality directly, since programmable multi-core graphics programming units are approaching a physical size that can fit within such a device. Others will not support such functionality, or will have a graphics/video pipeline that cannot easily be modified for flatscope purposes. However, provided such a PDA, cameraphone or other device supports fast two-way data transfer by a local connection, the necessary computing power can be included in another part of the whole system, for example, the base of the support frame. This embodiment of the present invention, therefore, ranges from a non-electronic adjustable support frame combined with software running on a hand-held PDA, cameraphone or other device, to a support frame (or other component) including a powerful digital system, and software running on the combination of the hand-held PDA, cameraphone or other device and the support frame (or other component).

Medical practitioners often track the progress of disease and healing by observing a sequence of photographs, taken over time. However, it is not easy in clinical conditions to arrange the same lighting for every photograph, so that a proper comparison may be made. If a body part is lit in a different direction or at a different distance from the light source, or if the sources vary between daylight and different types of light emitting system, changes between photographs may be difficult to assess.

The use of an imaging system according an embodiment of the invention for such photography can greatly reduce the problem. Firstly, the light sources 705 (see FIGS. 7*a* and 7*b*) can be bright, and dominate the picture, reducing problems with uncontrolled light sources. Secondly, each image can be automatically uploaded to the patient's electronic medical record (EMR). When any image subsequent to a first image is obtained, if the sequence is identified, the imaging system may download the first image and overlay it on the current image. Then, a medical practitioner can easily align the body part with its earlier position for a comparable photograph. Thirdly, in preferred embodiments, the lights 705 are physically arranged to have a range of spectra, so that the image obtained on a particular occasion includes measured brightness for several different kinds and levels of light. Fourthly, in preferred embodiments, the cameras 703 are multi-spectral in their image response. Fifthly, a standard object with well calibrated reflectivity at many frequencies may be included in each image that is obtained. With such data it is a straightforward problem in linear algebra to construct a least-squares fit to the physical reflectivity of the patient's surface at every visible point, in enough spectral detail to allow a highly accurate reconstruction of how the subject would appear in standardized light. This allows easy comparison. Moreover, if the full data set is retained, when an unexpected pathology becomes visible, the medical practitioner can revisit earlier images, with a filter adjusted to the spectral properties of different clinical precursors, as well as the current state. This may produce improved diagnosis. Much of this functionality is also available in the embodiment of the invention including a hand-held device. The support frame may be useful to standardize the camera position, as well as freeing the medical practitioner's hands to arrange the patient's position to match the rest of the series.

Another use of matching applies in the individualization of prosthetics. The latex surface of (for example) a prosthetic finger should match the appearance of the flesh hand it attaches to, in all forms of lighting likely to be encountered. Even within any one ethnic group, there is considerable variation in the reflected light off different skin colours. Classed by the human visual system into red, green and blue, two such reflected spectra of light originally from (for example) direct sunlight may appear identical, even though, in each band, different frequencies are stimulating the human brain's sensors. With other incident light (for example, a fluorescent bulb), a difference may also be present, but this may actually produce a visible difference in red, green and blue response. Material may appear matched in one lighting environment, but not matched in another lighting environment.

The adjustment of latex color consists essentially in adding a mixture of coloured materials, with a variety of different reflective spectra when embedded in the latex, to produce different proportions of the incident light reflected at each different frequency. The final reflectivity may be approximately a weighted sum of the spectra of these highly reflective materials (the weights being proportional to their quantity) and the reflection spectrum of the latex itself. Given reflectivity data for the skin in a substantial number of bands within the range of visible light, a least-squares calculation gives the set of weights on the material spectra that most closely combine to match the spectral responses in a standard set of lighting types. Convert those weights into grams of colourant per gram of latex, and the result is a material with a good match in all lights to the skin, in its current state.

Several different embodiments of the invention have been described, and each provide an improvement to known imaging systems described in the prior art.

It will be appreciated by a person skilled in the art that numerous variations and/or modifications may be made to the present invention as shown in the specific embodiments without departing from the spirit or scope of the invention as broadly described. The present embodiments are, therefore, to be considered in all respects to be illustrative and not restrictive.

The invention claimed is:

1. An imaging system comprising:
    image capture apparatus for capturing an image of an operator work site, the image including depth information; and
    display apparatus in communication with the image capture apparatus, the display apparatus comprising at least one display screen and being arranged to receive the image captured by the image capture apparatus, including the depth information, and display to the operator the image captured by the image capture apparatus, including the depth information, on the display screen;
    wherein the display screen is located between the operator's eyes and the position of the work site; and
    wherein the imaging system has real-time information of the position of one or both of the operator's eyes and the display apparatus is further arranged to display an updated image without distortion when viewed from the position of the one or both of the operator's eyes based on the real-time information, which is obtained by a tracking device worn by the operator.

2. The imaging system according to claim 1, wherein the image capture apparatus comprises a camera capable of obtaining depth information.

3. The imaging system according to claim 1, wherein the image capture apparatus comprises a plurality of cameras, and the depth information is obtained by comparing images captured by the plurality of cameras.

4. The imaging system according to claim 1, wherein the depth information is conveyed to the operator by management of the views delivered to each of the operator's eyes.

5. The imaging system according to claim 1, wherein the real-time information specifying the position of one or both of the operator's eyes is obtained by one or more cameras mounted on the imaging system together with analysis to locate the positions of the operator's eyes.

6. The imaging system according to claim 1, wherein the real-time information specifying the position of one or both of the operator's eyes is used to control zoom of all or part of the displayed image.

7. The imaging system according to claim 1, wherein the depth information is conveyed to the operator by parallax as the operator's head moves.

8. The imaging system according to claim 1, wherein the image capture apparatus comprises sensors for obtaining the image by detecting light in or in and around the visible range.

9. The imaging system according to claim 1, wherein the image capture apparatus comprises sensors for obtaining the image by detecting radiated or transmitted infrared radiation.

10. The imaging system according to claim 1, wherein the image capture apparatus comprises ultrasound emitters and sensors, and the display apparatus is enabled to display the image on the display screen, such that the work site appears to the operator to be at a location substantially corresponding to the position of the work site.

11. The imaging system according to claim 1, wherein the image capture apparatus is arranged to obtain the image by magnetic resonance imaging (MRI).

12. The imaging system according to claim 1, wherein images obtained by at least two modes are combined to form the image displayed to the operator on the display screen, the two modes being from a set including but not limited to visible light, magnetic resonance, ultrasound and infrared radiation.

13. The imaging system according to claim 1, wherein the display screen is arranged to display supplemental images.

14. The imaging system according to claim 1, wherein detected positions of a tool or tools controlled by the operator or operators provide input to the imaging system.

15. A method for capturing and displaying an image of an operator work site, the method comprising the steps of:
   capturing the image of the operator work site, the image including depth information;
   communicating the captured image, including the depth information, to display apparatus comprising a display screen;
   capturing real-time information of the position of one or both of an operator's eyes, the real-time information being obtained by a tracking device worn by the operator; and
   displaying to the operator an updated image derived from the captured image and the real-time information, including the depth information, on the display screen located between the operator's eyes and the position of the work site, which is arranged to display the updated image without distortion when viewed from the position of the one or both of the operator's eyes.

16. The method according to claim 15, wherein the step of capturing the image comprises obtaining the depth information by a camera capable of obtaining depth information.

17. An imaging system comprising:
   a display screen for displaying an image to an operator;
   means to obtain real-time information specifying the position of one or both of the operator's eyes, the real-time information being obtained by a tracking device worn by the operator; and
   means to use changes in the position of the operator's eyes to control magnification of all or part of the displayed image so as to display an updated image without distortion when viewed from the position of the one or both of the operator's eyes based on the real-time information.

18. The imaging system according to claim 17, wherein the display screen shows images stereographically, by showing different images to each of the operator's eyes.

19. The imaging system according to claim 17, wherein the display screen shows images with parallax, by adjusting the image according to the position of the operator's eyes.

20. An imaging system comprising:
   motion capture apparatus for capturing motion of manipulated tools;
   means to obtain real-time information specifying the position of one or both of an operator's eyes and worn by the operator; and
   display apparatus in communication with the motion capture apparatus, the display apparatus comprising at least one display screen and being arranged to receive the motion data captured by the motion capture apparatus, and display to an operator the motion captured by the motion capture apparatus, in the form of images on the display screen;
   wherein the display apparatus is further arranged to display additional images on the display screen based on the real-time information, the additional images being displayed without distortion when viewed from the position of the one or both of the operator's eyes; and
   wherein the display screen is located between the operator's eyes and the position of an operator work site.

21. The imaging system according to claim 20, wherein the additional images comprise images of a recorded procedure performed on real or virtual objects by another operator.

22. An imaging system comprising:
   a hand-held device comprising
   a camera on a first side for capturing an image of an operator work site, the image including depth information; and
   a display screen on a second side opposite the first side, for displaying to an operator the image captured by the camera, including the depth information;
   means to obtain real-time information specifying the position of one or both of the operator's eyes and worn by the operator; and
   support means for positioning the hand-held device between the operator's eyes and the position of the work site,
   wherein the display screen is further arranged to display an updated image without distortion when viewed from the position of the operator's eyes, based on the real-time information.

23. The imaging system according to claim 22, wherein the camera of the hand-held device comprises a camera capable of obtaining depth information.

24. An imaging system comprising:
   image capture apparatus for capturing an image of a subject, for detecting light in or in and around the visible range, and classifying the captured light into more than three frequency bands;
   means to obtain real-time information specifying the position of one or both of an operator's eyes and worn by an operator; and
   computing means for determining from the captured image, the spectral reflectivities of the subject and the lighting conditions when the image was captured, and for producing a further image without distortion when viewed from the position of the one or both of the operator's eyes, in the more than three frequency bands, of the subject in user-specified lighting conditions, the further image being based on the real-time information.

* * * * *